(12) United States Patent
Delahanty et al.

(10) Patent No.: US 11,837,356 B1
(45) Date of Patent: Dec. 5, 2023

(54) MEDICAL IMPLANT SOFTWARE SYSTEMS AND METHODS

(71) Applicant: CraniUS LLC, Baltimore, MD (US)

(72) Inventors: Conner Delahanty, Baltimore, MD (US); Tiger Gao, Baltimore, MD (US); Maximilian Zinkus, Baltimore, MD (US); Simone Bliss, Baltimore, MD (US); Rahul Gangwani, Baltimore, MD (US); Isaac Lefkovitz, Baltimore, MD (US); Vivian Looi, Baltimore, MD (US); Aayush Gandhi, Baltimore, MD (US); Owen Friesen, Baltimore, MD (US); John Cai, Baltimore, MD (US)

(73) Assignee: CraniUS LLC, Baltimore, MD (US)

(*) Notice: Subject to any disclaimer, the term of this patent is extended or adjusted under 35 U.S.C. 154(b) by 0 days.

(21) Appl. No.: 18/306,327

(22) Filed: Apr. 25, 2023

Related U.S. Application Data

(60) Provisional application No. 63/355,262, filed on Jun. 24, 2022.

(51) Int. Cl.
*G16H 40/40* (2018.01)
*G16H 80/00* (2018.01)
*G16H 40/67* (2018.01)

(52) U.S. Cl.
CPC ............. *G16H 40/40* (2018.01); *G16H 40/67* (2018.01); *G16H 80/00* (2018.01)

(58) Field of Classification Search
None
See application file for complete search history.

(56) References Cited

U.S. PATENT DOCUMENTS

| | | |
|---|---|---|
| 2011/0289497 A1 | 11/2011 | Kiaie et al. |
| 2015/0206408 A1 | 7/2015 | LaLonde et al. |
| 2016/0232010 A1* | 8/2016 | Dicks ............... G16H 40/67 |
| 2016/0366112 A1 | 12/2016 | Gropper |
| 2017/0100036 A1 | 4/2017 | Cinbis et al. |
| 2022/0134117 A1 | 5/2022 | Woock et al. |

OTHER PUBLICATIONS

International Search Report and Written Opinion dated Jul. 26, 2023, in corresponding International Application No. PCT/US2023/20656, 10 pages.

\* cited by examiner

*Primary Examiner* — Cai Y Chen
(74) *Attorney, Agent, or Firm* — Maier & Maier, PLLC (57) ABSTRACT

A method for remotely updating the behavior and state of a medical device or the firmware itself of a medical device, not requiring physical access to the device, that occurs through an encrypted and authenticated communication channel. The behavior and state of the device may be modified from a healthcare provider interface through a transmission method. The firmware of the medical device may be modified by the use of over the air device firmware updates, created from a designated secure machine called a build machine described herein. Both actions are transmitted to a server and then forwarded to a companion device and are particularly designed so that the server never stores sensitive cryptographic material in the event of server compromise. The companion device forwards the update to the medical device, which decrypts and validates the update or command before performing the change.

16 Claims, 5 Drawing Sheets

Fig. 5

MEDICAL IMPLANT SOFTWARE SYSTEMS AND METHODS

BACKGROUND

The use of drug delivery implants has reduced required and/or repetitive surgeries, targeted specific areas of the body, thereby increasing drug safety and efficacy, and eased the process of providing lifesaving medicine; such as when, for example, surgery is deemed suboptimal and/or less effective, like with chronic disease management and/or when systemic/oral medicine dosing is ineffective in crossing a homeostatic cellular barrier (i.e. blood brain barrier) and reaching the target organ or tissue. However existing medical implants are limited in their ability to monitor and control the implants various components by a number of factors.

First, medical implants have a heightened need for security and robustness of firmware or software, as if a bug were to occur or an unauthorized person were to gain access to the medical implant there could be disastrous or even lethal consequences to the patient. Second there is a need to reduce or eliminate the need to physically access the medical implant for updating, controlling, or restoring compromised components, as physically accessing the device may require the patient to undergo a costly and potentially dangerous surgery. Many existing devices are not able to sufficiently address these challenges, and therefore must greatly limit their reliance on software or firmware, which decreases the potential effectiveness of the device.

SUMMARY

In some embodiments a method for remotely updating a medical device may be provided. The method may include providing build information to a build machine and receiving cryptographic key information as well as a link that may return cryptographic material or perform cryptographic operations (such as encryption, decryption, signing, validation, or other operations) with this cryptographic key (key path). The build machine may then create a medical device update. A server may receive companion device information where the companion device is associated with the medical device. In some embodiments performing the operations or retrieving the keys made available by the key path may be restricted to only the companion device, and may be done either directly or via route of the server. A key management system (KMS) may send a cryptographic certificate to the build machine either directly or via route of the server, which may certify and encrypt the medical device update with the cryptographic key information. The encrypted medical device update and companion device information may then be transmitted to the server which may then send a notification to the patient-facing application. The companion device may then access the patient-facing application, perform over the air update operations, and download the encrypted medical device update from the server. The companion device may transmit the medical device update to the medical device which may decrypt and validate the medical device update.

In some embodiments a system for remotely updating a medical device may be provided. The system may include a medical device and a companion device associated with the medical device. The system may further include a server that may send companion device information to a build machine and a KMS which may send a cryptographic certificate to the build machine. The build machine may receive at least build information and a link that may return cryptographic material or perform cryptographic operations. The build machine may then create a medical device update and certify and encrypt the medical device update with the cryptographic certificate. The build machine may transmit the medical device update and companion device information to the server. The server may further send a notification to a patient-facing application that is accessed by the companion device and performs over the air update operations. The companion device may then download the encrypted medical device update from the server and transmit the medical device update to the medical device which may then decrypt and validate the encrypted medical device update.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

In one or more exemplary embodiment a medical implant device may be provided. The medical implant may be, for example but not limited to, a cranial medical implant, a knee implant, a spinal implant, etc. The medical implant may perform the function of, for example but not limited to, delivering medication, monitoring conditions of the body, etc.

In an exemplary embodiment firmware may be implemented on a processor or microcontroller, which may control the medical implant device. The medical implant device and related firmware may be able to support various forms of communication, including for example low energy Bluetooth (BLE) wireless communication, Wi-Fi communication, device firmware over the air update (DFU OTA) functionality, or any other communication methodology known in the art. The firmware may support a variety of functionalities, including but not limited to; controlling wireless connections and communication; reading medical implant sensors; controlling the medical implant to dispense medication through, for example, pumps; data storage and encryption; and/or safety and status reporting.

In an exemplary embodiment systems and methods to securely retrieve and store data on the medical implant may be provided. The firmware may be contained in one or more sub systems, for example but not limited to, a communication control sub-system (CCS), a sensors control sub-system (SCS), a pump control sub-system (PCS), a data storage sub-system (DSS), and/or a safety and status sub-system (SSS). Each sub-system may perform a specific action and/or collect data related to a specific action or system, and may communicate through a message passing system (MPS).

Figure 1:
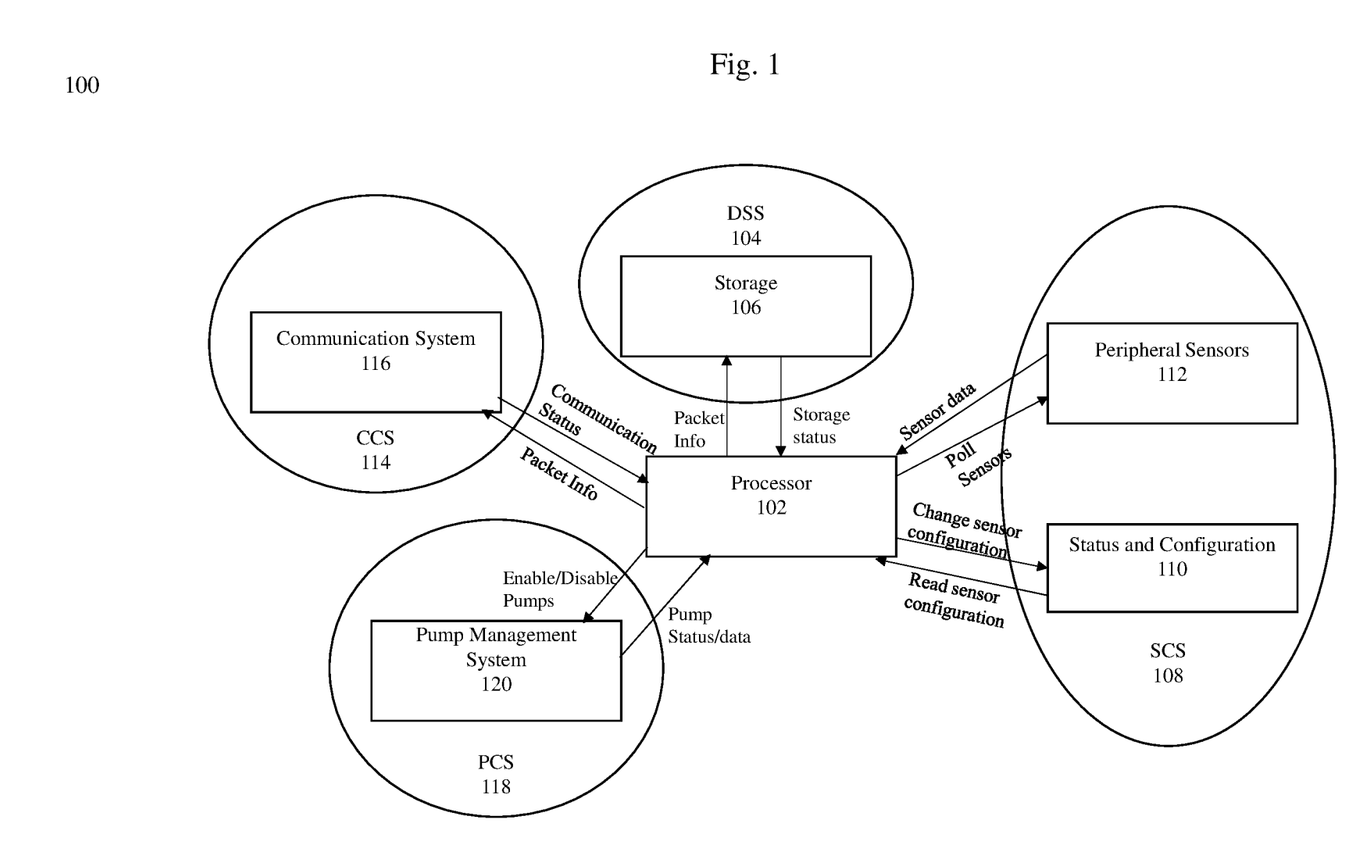
FIG. 1 is an illustration of sub-systems of an exemplary medical implant control system.

Referring now to FIG. 1, one or more exemplary subsystems of an exemplary medical implant control system 100 may be described. The exemplary control system 100 may include a processor 102. The exemplary control system may include the DSS 104 which may contain one or more storage elements 106, such as, for example, an electronically erasable programable read only memory (EEPROM) non-volatile storage. a ferroelectric RAM (FRAM), a flash storage device, a trusted platform module (TPM) etc. The processor 102 may send packet information to and may receive storage information from the one or more storage elements 106. The control system 100 may further include the SCS 108. The SCS 108 may include status and configuration information 110 such as, for example but not limited to, sensor configuration and sensor state, the processor 102 may enable reading of the status and configuration information 110 and may receive, for example, sensor resolution and reading frequency information from the status information 110. The SCS 108 may further include one or more peripheral sensors 112, which may include, but are not limited to, pressure sensors, temperature sensors, fluid level sensors, voltage levels, received signal strength indicators (RSSI) etc. The processor may send requests to poll the sensors 112 and may receive sensor data.

The control system 100 may further include the CCS 114, which may control communication systems 116, which may be, for example, BLE, Wi-Fi, LoRaWAN, or any other communication protocol. The processor 102 may receive communication status from and may send packet information to the communication system 116. The control system 100 may further contain the PCS 118, which may include a pump management system 120. The pump management system 120 may send pump status and pump data to the processor 102 and may receive enable or disable commands. It may be understood that in different embodiments not all of the subsystems described may be utilized, or additional subsystems may be utilized in addition to those described above.

One or more of the exemplary subsystems may now be explained in more detail.

The CCS may be responsible for overall connection and communication between the plurality of sub-systems and/or between the medical implant and one or more of a companion device, which may be for example a tablet, iPad, or other mobile device, a base station, or another computing element. The CCS functions may include, for example but not limited to, controlling the intervals at which to turn communication on and off, sending packets of data based on priority if a connection to multiple devices is established, receiving and processing commands from other devices, sending angle of arrival (AoA) to another device such as the base station through the advertising interval, handling multiple intervals of communication to multiple other devices such as the companion device and/or base station, and/or securing the wireless connection, such as when bonding with another device such as the companion device.

In an exemplary embodiment the CCS may determine when to turn on communication capabilities, for example when to turn on BLE, and connect with other devices, for example the companion device or the base station. In an exemplary embodiment the CCS firmware may not actively advertise a communication signal except during a specified transmission window, creating connection cycles of on and off behavior, which may aid in preserving battery life. The CCS may continue advertising during the specified transmission window until a connection is established and/or until a specified amount of time has passed. In some embodiments the specified time for the transmission window may be adjustable by external commands.

In an exemplary embodiment the CCS may be responsible for sending packets of data, which may be received from, for example the MPS. The packets of data may include, but are not limited to, sensor data, medication dispensing data, and/or safety and status data. The CCS may receive the packets of data as encrypted packets, and may send the encrypted packets to another device, for example the companion device. If a connection to the companion device is established, the packets of data may be sent to the companion device, and the DSS or other storage may additionally be queried for any earlier-stored packets or logging information that also need to be sent. In some embodiments if the connection to the companion device fails, or the communication advertising window closes, the data packets may instead be passed to the DSS or another storage element. Any communication marked for delivery that is not successfully sent may be attempted to be sent during the next connection cycle. In some embodiments if communication fails to send multiple times the advertising window may be progressively increased each cycle until the communication is successfully received.

In some embodiments the CCS may also transmit emergency packets, which may be packets that are created in response to safety and/or security errors that are detected on or by the device. When a safety or security error occurs the CCS may bypass the normal transmission procedure and may immediately connect to the companion device and transmit the emergency packets. If the CCS cannot connect to the companion device, the CCS may modify the priority of stored data and modify the transmission window frequency and timeframe, for example the CCS may attempt to re-transmit the information every minute or every five minutes.

In some embodiments the CCS may also be responsible for processing commands from the companion device. When the command is read the CCS may forward the command to another sub-system, for example the MPS.

Figure 2:
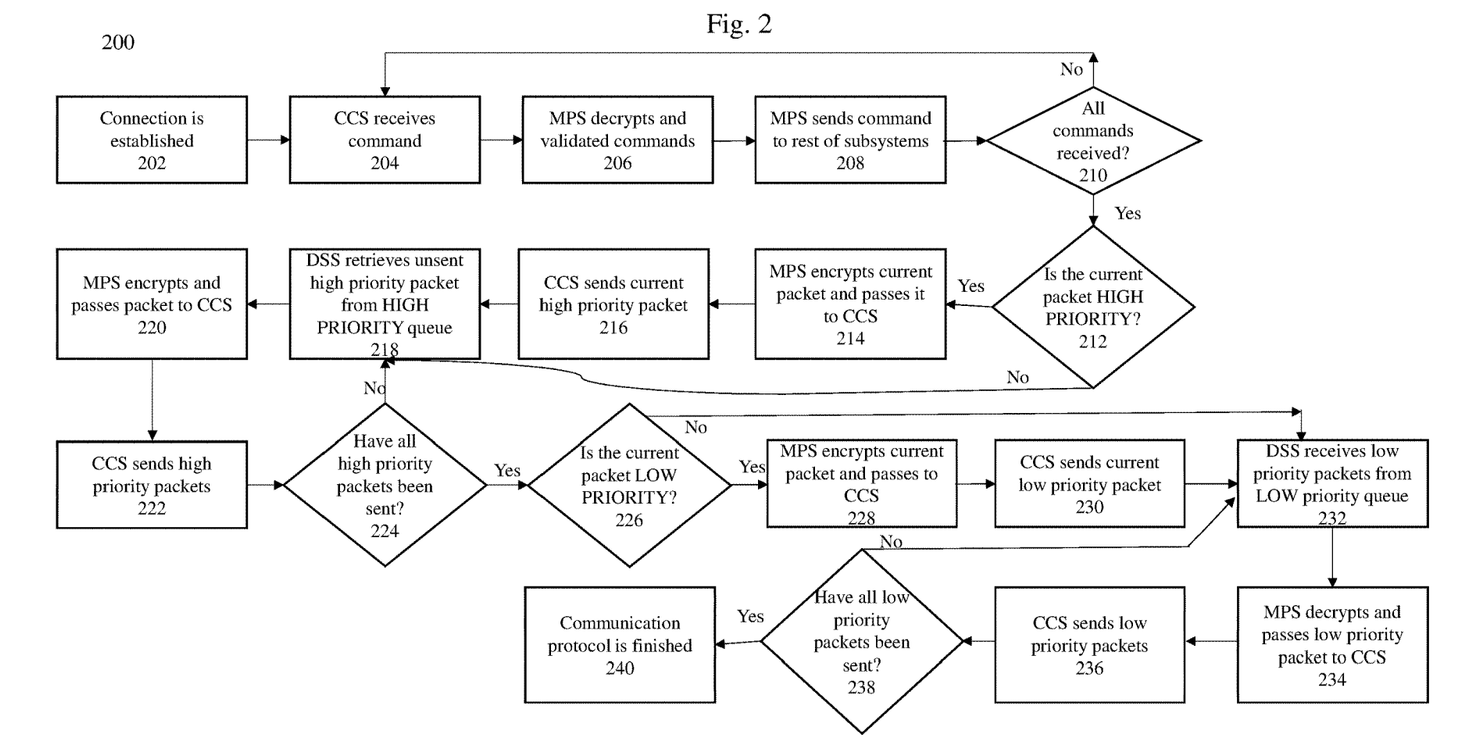
FIG. 2 is an exemplary prioritization communication flowchart.

In some embodiments the CCS may handle assigning priority for sending or receiving of data packets. Referring now to FIG. 2. an exemplary prioritization communication flowchart 200 may be shown and discussed. In a first step 202 a connection may be established between the CCS and the companion device, the connection may be, for example, a BLE connection. In a next step 204 the CCS may receive a command from the companion device. In a next step 206 the MPS may decrypt and validate the command. In a next step 208 the MPS may send the command to one or more of the other subsystems as relevant. In a next step 210 the CCS may check whether all commands have been received, if more commands are waiting then the CCS may return to 204, if all commands have been received then in a next step 212 the current packet may be assigned as high priority or low priority. If the current packet is not high priority the system may skip to step 218, if the current packet is high priority then in a next step 214 the MPS may encrypt the current packet and pass it to the CCS, and in a next step 216 the CCS may send the current high priority packet to the companion device. In a next step 218 the DSS may retrieve unsent high priority packets from the high priority queue. In a next step 220 the MPS may decrypt and pass the packets received from the DSS to the CCS. In a next step 222 the CCS may send the high priority packets. In a next step 224 the system may verify if all high priority packets have been sent, if not then the system may return to step 218, if all high priority packets have been sent then in a next step 226 it may be determined whether the current packet is low priority. If the current packet is not low priority then the system may skip to step 232, if the current packet is low priority then in a next step 228 the MPS may encrypt the current packet and pass it to the CCS. In a next step 230 the CCS may send the current low priority packet to the companion device. In a next step 232 the DSS may receive low priority packets from the LOW priority queue. In a next step 234 the MPS may decrypt and pass the low priority packets to the CCS. In a next step 236 the CCS may send the low priority packets. In a next step 238 the system may determine whether all low priority packets have been sent, if not then the system may return to step 232, if all low priority packets have been sent then the communication protocol may be finished in step 240.

In some embodiments the CCS may use multiple advertising sets to communicate with multiple devices. For example, a first advertising set may be used to communicate with the companion device and a second advertising set may be used to communicate with the base station. In other embodiments more than two advertising sets may be used to communicate with more than two other devices. In some embodiments two or more advertising sets may be advertised simultaneously.

In an exemplary embodiment the CCS may have bonding capabilities with one or more external devices. In an exemplary embodiment when the medical implant is first powered it may advertise a bonding service periodically, for example every 15 minutes or every hour. The bonding service may contain an encrypted number. The companion device may be programmed to listen for the advertising request from a specific implant and may bond with that implant in either a clinical or manufacturing setting. The companion device may read the value from the bonding characteristic, decrypt the encrypted number, and/or encrypt a validation number in its response. When the implant sends a correct validating response, the implant may bond or pair to the tablet. Once bonded the implant may switch to its normal advertising interval as discussed above. If the companion device fails to bond to the implant, or the connection is otherwise compromised, the bonding process may be repeated in a connection cycle, which may allow for re-bonding. Failure to pair may be reported to another sub-system such as the SSS, and may be reported as, for example, a security incident.

In an exemplary embodiment the SCS may be responsible for, for example, configuring and reading data from sensors and/or passing on sensor or anomaly data. In some embodiments sensor data may be stored in a data structure of pre-allocated maximum size. When data is ready for transmission, the data may be sent to the MPS to be appended to a packet structure, and then either transferred to the CCS for transmission or stored in the DSS if there is no connection. The SCS may be configured to read sensors on a certain frequency, which may be any time, for example every second, every minute, or every 15 minutes. The frequency at which the sensors are read may also be dynamic or adjusted based on commands. In some embodiments the SCS may have a separate set of logic to control the interval of RSSI readings depending on the mode the implant is set to, for example a first set of logic may be used for a tracking mode while a second set of logic is used for a charging mode.

In an exemplary embodiment the PCS may be responsible for, for example, controlling one or more medication dispensing mechanisms within the medical implant. The PCS may ensure that the medication dispensing cycles are controlled in accordance with a desired distribution or flow rate, considering other implant and distribution system parameters. The PCS may also send data related to the medication dispensing system for inclusion in any external communication, for example to the paired companion device. The medication dispensing system data may be sent to the MPS to be packaged into a packet structure, and then either transferred to the CCS for transmission or stored in the DSS if there is no connection.

In an exemplary embodiment the DSS may be responsible for, for example, dealing with long-term storage and retrieval of important device data, such as logs, packets, and the current status of the software, firmware, or hardware systems. The DSS may read and write logs and packets and may be capable of doing bulk returns on these values. In some embodiments some or all of the DSS data may be encrypted. In some embodiments the DSS may use an erasable programmable read-only memory chip (EEPROM) to read and write data, and the data stored in the DSS may be split according to different criteria or categories, for example metadata, application state, emergency packets, low priority packets, low priority logs, etc. In an exemplary embodiment any failures related to storing or retrieving information in the DSS may be reported as a safety issue, and any issues with encryption and decryption may be reported as a security issue.

In an exemplary embodiment, if a critical battery threshold is reached, the DSS may store the application state of the implant and all sub-systems, and then disable some or all of the sub-systems, for example the SCS battery and RSSI measurement systems may be left enabled while all other sub-systems are disabled. Any data may be transferred to the DSS for storage and external communication may be disabled. When a restore threshold is reached, the SSS may trigger the restoration of the state saved by the DSS, and all sub-systems may resume operation. In some embodiments some sub-systems may be restored in a disabled state and require re-enablement, for example the PCS may be restored in a disabled state and require re-enablement from the CCS. The critical battery threshold and restore threshold may be updated over time to, for example, account for performance degradation of the battery, and may be updated based on, for example, a known battery consumption model used by the companion device and/or base station.

In an exemplary embodiment the SSS may be responsible for the safe operation of the implantable medical device, for flagging or recording abnormal behavior, handling status information, and interpreting sensor values. Flagging and/or recording abnormal behavior may include, but is not limited to, detecting abnormalities, creating alerts or errors, and/or elevating alerts or errors. In some embodiments when a subsystem detects an anomaly it may inform the SSS of the anomaly, and the SSS may categorize this information into one of a plurality of categories. In some embodiments the categories may be based on the cause and/or severity of the anomaly, and categories may include, but are not limited to, informational, performance, safety, and/or security.

In an exemplary embodiment informational anomalies may include, for example, single read failures, low battery power, or informational logs. When an informational anomaly is detected the SSS may send the anomaly information to a connected companion device or base station and/or may store the log information in the DSS. In some embodiments informational anomalies may be observed and tracked in order to identify trends.

In an exemplary embodiment performance anomalies may include, for example, storage failures or sensor read failures. When a performance failure is detected the SSS may update the appropriate bits in the status register for each performance anomaly and send or store that information in the DSS. In some embodiments, in response to a detected performance anomaly a major response error protocol may be instituted, and/or an over the air update may be sent.

In an exemplary embodiment safety anomalies may include, for example, rapid pressure changes, drug measurement failures, or CCS failures. When a safety anomaly is detected the SSS may send a separate emergency packet immediately, or the companion device may institute a security anomaly alert if the connection between the companion device and implant is compromised. In some embodiments, in response to a safety anomaly a critical error response protocol may be implemented, which may include, for example, re-implantation of the medical implant.

In an exemplary embodiment security anomalies may include, for example, invalid command authentications. When a security anomaly is detected the SSS may send a separate emergency packet immediately to the DSS for transmission. In some embodiments, in response to a security anomaly a security event response protocol may be implemented which may be, for example, monitoring.

In an exemplary embodiment the MPS may be responsible for, for example but not limited to, handling encryption and decryption of packets, serializing and deserializing packets into byte arrays for communication or storage, allocating data from each subsystem into packets, processing and validating commands and letting subsystems know of incoming commands, and/or determining if the firmware is in tracking or charging mode. In some embodiments the firmware may be built on a model that allows for the subsystems to respond and perform functions independently. The MPS may help coordinate the operator of each subsystem by handling communication between the subsystems.

In an exemplary embodiment the logic of one or more sub-systems may be abstracted to one or more timers. For example, a first timer may read sensors (such as, for example, pressure, temperature, volume, battery, and/or RSSI sensors), a second timer may create data packets to either be sent or stored, and a third timer may control a medication delivery mechanism such as the pump. It may be understood that in other embodiments more or fewer timers may be used, and the sub-systems may be distributed differently depending on the application.

In an exemplary embodiment the firmware may operate off an embedded system clock. In some embodiments a time synchronization method may be used in order to correct the system clock as it becomes out-of-sync with real world time.

An exemplary time synchronization method may involve the firmware receiving a baseline coordinated universal time (UTC) upon communicating with a patient-facing application. Periodically, as defined by a timesync interval, the companion device may post the current UTC, and the firmware may adopt the posted time and synchronize its internal counter to that time. The synchronization method may particularly be used in power down scenarios where a significant discrepancy may be introduced into the internal clock while powered off. It may be understood that in some embodiments all of the systems may be able to run on a timer accurate to the nearest second, rather than requiring sub-second accuracy. Therefore, periodic syncing of the method described above may be sufficient to maintain an accurate clock, and more power intensive methods of syncing may be avoided.

Figure 3:
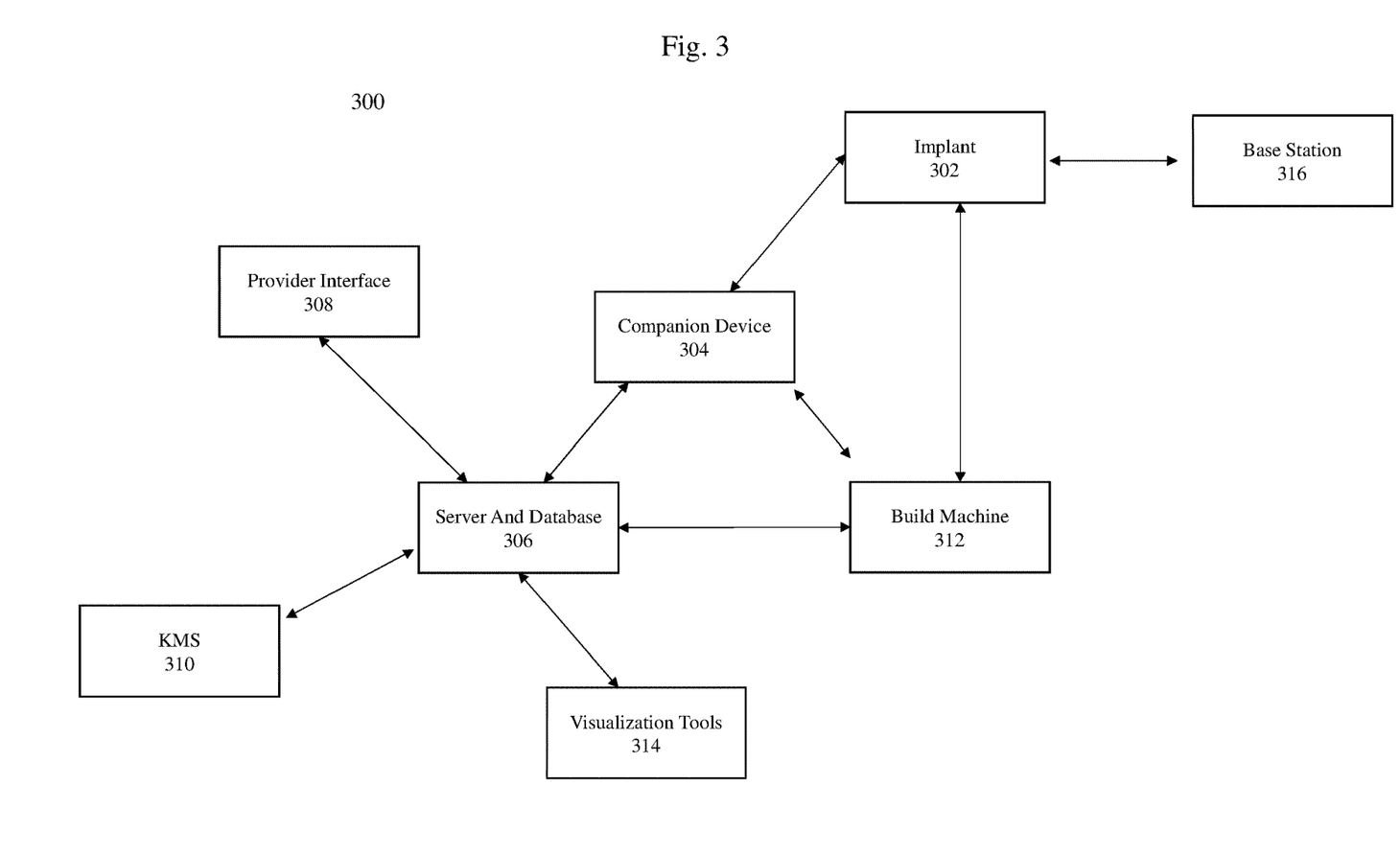
FIG. 3 is an exemplary illustration of interactions between the medical device and related firmware platforms.

In some embodiments one or more other software platforms may interact with the medical implant. Referring to FIG. 3 interactions between the medical device and exemplary related software platforms 300 may be shown. The software platforms 300 may include, but are not limited to, a medical implant 302, a companion device 304, a server and database 306, a provider interface 308, a key management system (KMS) 310, build machines 312, and/or visualization tools 314.

In some embodiments the medical implant 302 may send status packets, logs and/or emergency packets to the companion device 304 and may send constant tone extension (CTE) signals to the base station 316. In some embodiments the companion device 304 may send commands, time sync data, and/or DFU OTA's to the implant 302, and may send status packets, logs and/or emergency packets to the server and database 306. In some embodiments the server may send commands, DFU OTAs, and/or alerts to the companion device 304, encrypted commands to the provider interface 308, and/or implant-companion cryptographic keys, certificates, and/or private keys to the build machine 312.

In some embodiments the provider interface 308 may send commands to the server and database 306 and ultimately to the KMS 310. The commands sent to the KMS 310 may then be encrypted by the KMS 310. In some embodiments the KMS 310 may transfer cryptographic keys to the companion device either directly or via route of the server and database 306. The KMS 310 may act as a proxy to the server 306 for increased security. The KMS 310 may send encrypted commands to the provider interface 308 and may send cryptographic keys, certificates, and/or private keys to the build machine 312, both either directly or via route of the sever and database 306. The build machine 312 may send code and cryptographic keys to the implant 302, and code, certificates, and/or private keys to the companion device 304. The build machine 312 may further send companion device info and/or companion device assignment info to the server 306, and companion device and/or implant universal unique IDs (UUIDs) to the KMS 310 either directly or via route of the server and database.

In some embodiments a tracking mode may be used when, for example, the medical implant is attempting to establish a connection with an external system, such as the base station. While the advertising window is open, the firmware may send Constant Tone Extension (CTE) signals to the base station or other external system such as the base station. When the window closes, the CCS may notify the SCS through the MPS that a tracking mode has been entered, and may read the RSSI to establish a baseline RSSI value. After a pre-determined amount of time, for example 10 seconds, 15 seconds, a minute etc, the SCS may read the RSSI again to determine the value has increased relative to the baseline RSSI value. If an increase is detected, the SCS may notify the MPS that charging mode has been entered. When the implant enters the charging mode the SCS may periodically read the RSSI to determine whether the implant is being charged. If RSSI decreases below a predetermined threshold, the implant may return to a default mode.

In one or more embodiments a patient-facing application may be included. The patient-facing application may be installed on, for example, the companion device, and may, for example, serve as a router that connects the medical implant to a server, act as a processor that processes and interprets implant data, and/or act as a patient interface for the patient to interact with the medical implant. The companion device may be enrolled with a device management application that may restrict network connectivity, device functionality, and/or device settings for security or compatibility reasons. For example, in an exemplary embodiment only basic accessibility preferences such as text size, brightness, etc may be freely modified from the companion device. In an exemplary embodiment network connectivity may be limited to communication with allowed resources, such as the medical implant and related resources, resources related to application or device functionality, etc, and Bluetooth and/or internet connectivity setting may be set to always be enabled.

The patient-facing application may have a plurality of functionalities, including but not limited to, facilitating communication between the implant and the server, processing data received from the implant and the server, storing data received from the implant and the server if a connection is disrupted or otherwise unavailable, and/or displaying information to a user or patient. The patient-facing application may include a plurality of architectural components including, for example, a notification service, a client service, an implant connection management service, a key service, a data processing service, a data reliability service, and/or a plurality of UI components.

In an exemplary embodiment, updates to the patient-facing application may be applied using a mobile device management application. While an update is being applied it may be understood that the application may be unable to receive information from or send information to the implant. In order to mitigate these issues, the implant's reliability functionality may ensure that packet loss is minimized or eliminated, and further any commands sent to the companion device may result in a response sent to the server to confirm that the command was received. If the response is not received by the server, for example due to the updating process, a recovery response may be initiated.

In an exemplary embodiment, the base station may power the implant through object tracking and antenna steering. The base station may have a plurality of operating states, for example there may be a default mode, a tracking mode, and/or a charging mode. The default mode may be used when the medical implant is being used in normal operation, and the AoA service may be set at the default advertising window. The implant may start in a default mode and may advertise to the base station to seek a connection at set intervals. The advertising window for the base station may be separate and unrelated from the advertising window for the companion device. When a connection between the implant and the base station is established the implant may enter a tracking mode, which may involve, for example, sending CTE or another signal type which can be received by a base station antenna array to determine relative position. In some embodiments the base station firmware may isolate the connectivity, tracking, and beam-steering components of the system.

In an exemplary embodiment historical data on devices and logs may be stored in a database. The database may additionally help maintain the state of commands for ongoing systems. In an exemplary embodiment a server may provide a standard way to adjust database information and may act as a network bridge or an API retrieval source for other software platforms, for example the patient-facing application, provider interface, and/or dashboards or other visualization tools. In some embodiments the server and database may communicate on a shared virtual private cloud, which may allow for local network connection. The database may not be publicly accessible and may only accept access from the server or server's IP address. The database may have two accounts, a root account, and an account with read/write to table permissions, which may operate the corresponding server instance.

In some embodiments the server may utilize inputs to perform operations, the inputs may include, but are not limited to, path parameters, request headers/data, and/or query parameters. The operations that utilize the inputs may include, but are not limited to, read operations, write operations, and update operations to the database. Database operations within an endpoint may be bundled in transactions, which may ensure that the transaction is an atomic operation. Endpoints may return a response, including for example a response code and/or potential data.

In an exemplary embodiment the provider interface may allow healthcare providers to adjust characteristics of the medical implant without requiring physical access to the device. The provider interface may be provided on a provider device, which may be, for example, a computer, a web browser, a tablet, an iPad, or any other computing element. In some embodiments this may allow the implant to be compatible with telehealth environments and may assist in protecting the medical implant against physical attacks from, for example, magnets or wands.

The provider interface may be composed of several sub-units, including but not limited to authentication, associated patients, command issuing, and/or real time command statuses. In an exemplary embodiment command issuers may be restricted to specific patient devices, as determined by a central patient index. The index may be stored in the server's database and may only be alterable by specific authorized systems. The central patient index may be updated internally during, for example, the distribution of a device to a patient and provider. In some embodiments there may be a two-layer authentication system. The first layer may be, for example, a device level authentication system, where biometrics, pins, and/or passwords may be required to access the device. The second layer may be, for example, a VPN security layer, where in order to access the required VPN a multi factor authentication system will need to be used. Additionally, the provider may need to periodically reauthenticate when using the device, for example authenticating after login, and also before any command is sent, and/or periodically based on time, e.g. every 5 or 10 minutes.

In an exemplary embodiment command issuers may view and select their patients from the provider interface. Restrictions on the server side may be applied so that command issuers are limited to viewing only their patients. The provider may be able to view all of their patients through a display, and based on permission may be able to see further information on specific patients, for example but not limited to, patient name, contact information, address, and/or picture. Patient related alerts or requests for contact may be available on one or both of the general patient display or the specific patient display.

In an exemplary embodiment the provider interface may format commands to send to the server, encrypt commands with the KMS, transmit commands to the server, and/or update UI elements when a command status is updated. The provider interface may also issue real time command statuses, as after sending a command, the command issuer may need to know that the command was successfully executed.

In an exemplary embodiment the KMS may perform key lifecycle management, which may include the creation, destruction, storage, and/or distribution of cryptographic material in order to support cybersecurity of the medical implant and related systems. The KMS may be implemented on multiple different systems. The KMS may be divided into two parts, one part may exist in a physical device, such as a physical hardware security module (HSM), while a second parts exists in a virtual space such as Amazon Web Services or similar cloud environments. Less sensitive material, for example the parts of the KMS that handle cryptographic keys, or the compute logic servicing, may be hosted in the virtual environment. More sensitive material, for example root certificate signing keys, may exist in the HSM.

In an exemplary embodiment one or more build machines may administer the initial deployment and subsequent updating of the medical implant device and companion devices. The build machines may be a physical device located in a secure location and may interface with the physical and/or virtual aspects of the KMS to manage certificates. In some embodiments the build machines may handle the initial flashing, preparation, and configuration of the medical implant boards before installation of the boards. The build machines may also communicate the creation of the boards and their configurations to the server and may pair the medical implant with a companion device, for example by creating a QR code for the companion device to use to retrieve the appropriate keys for communicating with a specific medical implant board.

The build machines may also handle DFU processes. The build machines may build the DFU package, get the package signed by a DFU key, encrypt and store the packages, and/or inform the server to notify the companion device to retrieve the package to begin updating the medical implant.

In some embodiments there may be one or more separate companion device build machines for the companion device. The companion build machines may perform the initial configuration of the companion device so the companion device may have the necessary configuration profiles and mobile device management systems installed. The companion build machines may interface with a certificate administration interface to create certificates for the companion device. The initial companion device provisioning process may require physical access to the companion device. The companion build machines may also build application packages and updates for the companion device.

In an exemplary embodiment one or more visualization tools may be used to visualize information about the medical implant. Visualization tools may include, for example, a data dashboard, a fleet management system, a server API client, etc. The visualization tools may include information on, including but not limited to, alerts, summary statistics, medical implant PCBs, medical implant or related systems tests, diagnostics and statues, status and/or statuses of commands or updates. These tools may access the server in order to obtain information, and may be used by, for example, engineers or developers in order to obtain general information on the medical implant system operations. In some embodiments the data may include averages, means, standard deviations, or other aggregations of a plurality of medical devices, or data related to a specific device's current state or earlier states.

In some embodiments, these tools may include a GUI or other display which may visually show the data. Some examples of data that may be recorded or shown include, medical device fluid levels, battery charge or lifetime, medical implant fluid pressure, medical implant fluid type, medical implant implantation location, etc.

In an exemplary embodiment communication between the companion device and the server may be facilitated using, for example, push notifications and/or HTTP requests. The patient-facing application may receive commands, keys, and other information via, for example, push notifications. These notifications may be processed and acted on using, for example, a notification service, which may parse the notifications payload and perform the appropriate action via the corresponding function. The patient-facing application may support multiple categories of push notifications, such as callback requests where the server sends a URL from which the patient-facing application can request additional data from the server or alerts which may trigger pop-ups, alarms, sounds, or other notifications of the companion device. Callback requests may come in a variety of forms, and may include payloads on the assigned patient, the board assignment, on commands, on the device firmware update (DFU), or on storage erasure. In some embodiments the patient-facing application may send and receive data through a client service.

A notification with an assigned patient payload may trigger a function that uses a Key Service, responsible for handling any interactions with a secure storage system, such as securely storing new patient information. Passing an invalid action may result in no action being taken, and a security event may be noted and reported to the server. A notification with a board assignment payload may trigger a function that uses the Key Service to save a new key and board information to secure storage. A notification with a command payload may trigger a function to store a command for later transmission to the implant, or to execute a command on the companion device.

A notification with a DFU payload may trigger a function that stores the downloaded encrypted DFU firmware executable to the application's secure file system and notifies the user on the UI that a DFU update is pending. A notification with an erase storage payload may trigger a function to erase everything in some or all forms of persistent storage—for example any persistent secure or unsecure storage, and/or the file system.

In an exemplary embodiment communication between the medical implant and the companion device may be facilitated through an implant connection management service (ICMS). In an embodiment, the ICMS may periodically listen for advertising from the implant in order to connect to the implant. The ICMS for a particular patient-facing application may be restricted to only looking for advertisements from one or a specific subset of implants to which it is assigned. The initial assignment may be, for example, during a registration process or through push notifications.

In some embodiments the patient-facing application may route OTA DFU's or commands sent by the server or another interface to the medical implant. When a connection with the medical implant is made, the patient-facing application may check local storage for pending commands, validate the command's expiration date, reject and/or inform the server of expired commands, and/or encrypt the command with a cryptographic key and transmit the command over the data/command characteristics. In some embodiments for over the air DFU's a DFU firmware executable may be received from the server, which the patient-facing application may store in local storage. When a connection with the medical implant is made, the patient-facing application may retrieve the OTA DFU, decrypt it with a private key, validate the update expirations date, and/or send the firmware executable over the implant's DFU characteristic. In some embodiments the patient-facing application may notify the user and/or server of the result of the update.

In an embodiment the implant may send packets and logs to the companion device, which the patient-facing application may route to the server. Packets may first be decrypted and parsed before being sent. In some embodiments, if a parsing failure is detected, the data may still be sent as decrypted but unparsed, and a notification that the data is unparsed may be included.

In some embodiments parsing and interpretation of data sent by the implant may be limited to the patient-facing application, which may minimize logic duplication. The server application logic may be restricted to, for example, simple operations like unit conversion, and the companion device may handle all other processing such as converting raw values to readable values, determining alerts, etc. If the patient-facing application's logic determines that an alert should be raised, it may trigger a UI alert notifying the user, and/or may pass the parsed data up to the server with information about the alerts triggered. The server may then act in accordance with the patient-facing application's determination of the alert.

In some embodiments if the parsing or decryption on the patient-facing application fails, the patient-facing application may send the unparsed or unencrypted data to the server, along with an indication of the failure to parse or encrypt as an error. The user may also be notified of the failure via the patient-facing application or other UI elements.

In some embodiments operation of the implanted medical device may involve functionality that occurs across multiple software platforms, for example via the transmission of status packets. The interaction between these multiple platforms may be understood as data flows, which may include, but are not limited to, the sending and receiving of status packets, commands, implant errors, DFU OTAs, cryptographic material for implant—patient-facing application communication, certificate update and replacement, over the air update of the patient-facing application, flashing, and/or defining device and manufacturing information. It may be understood that in some embodiments certain platforms may be restricted to sending or receiving data flows to specific other platforms.

In an exemplary embodiment status packets and logs may originate in the implant, and may include, for example but not limited to, pump data, sensor readings, status data, and/or indication of time accuracy. The status packets may then travel to the companion device and may be decrypted and parsed. The patient-facing application may use the status and most-recent sensor data to display data to the patient. The rest of the data may be sent to the server to be parsed and stored in separate models for each data entry. The data may be analyzed by dashboards or other visualization tools.

In an exemplary embodiment commands may originate from a physician or other authorized person, who may, for example, enter the command information through a GUI. The command may then be formatted and encrypted, for example with an ephemeral symmetric key through KMS. The provider interface may then be sent the encrypted command and an encrypted ephemeral key. The encrypted command and key may then then be sent to the server, the server may verify or acknowledge receipt, for example by sending the provider interface a code. The command may be stored in the database and may have a corresponding status, for example "server_received" or "queued_for_transmission". The server may then communicate to the companion device that a new command was issued. The request may then be approved by the patient or user through the patient-facing application, in some embodiments the clinician may also be required to approve the request, for example by inputting a unique numerical code. Once the requisite approvals have been given the command may be decrypted and stored in the patient-facing application's local filesystem. The next time a connection between the companion device and the implant is established, the command may be transmitted to the implant, decrypted by the implant, and instituted.

In an exemplary embodiment, when an error occurs on the implant, the error may be captured in the status, or as a log. The status and/or log may be sent to the patient-facing application and displayed as necessary and forwarded to the server for processing. In some embodiments the errors may trigger one or more alert systems, in accordance with an error response protocol for the relevant error class.

In some embodiments the companion device may be configured to give visual or auditory alerts based on transmitted medical implant data. There may be a plurality of predetermined or adjustable thresholds for the medical implant based on a variety of factors, for example low battery state, low medication in the medical implant, patient abnormalities detected by the medical implant sensors, etc. In some embodiments alerts may be tied to a determination that the medical implant has been compromised. Determinations that the implant has been compromised may include, for example, detection of failed OTA cryptographic verification, failed command cryptographic verification, commands that pass verification but are repeats of previously used commands (i.e. the ID number of the command is an already used ID number), there is a mismatched firmware signature, and/or there are decryption issues that might indicate the cryptographic key has been comprised. In some embodiments alerts may be tied to a determination that the patient app has been comprised. Determination that the patient app has been comprised may include, for example, detecting failures in the app allowing someone to access the app code and forge data and/or failure for the app to pass a signature check on boot up. In some embodiments the auditory or visual alerts may be given if the companion device is not connected to the internet, and the alerts may include beeps, buzzing, flashing lights, push notifications, etc. In some embodiments the alerts may be given continuously or periodically until acknowledged by the user. The relevant data may also be held by the companion device until a connection with the internet is reestablished, which may happen automatically at the time an internet connection is established. After the connection is reestablished, the companion device may attempt to periodically fetch data from the server.

Once the companion device connection to the server is re-established, the server may then forward the alerts and related data to healthcare providers or other relevant personnel.

Figure 4:
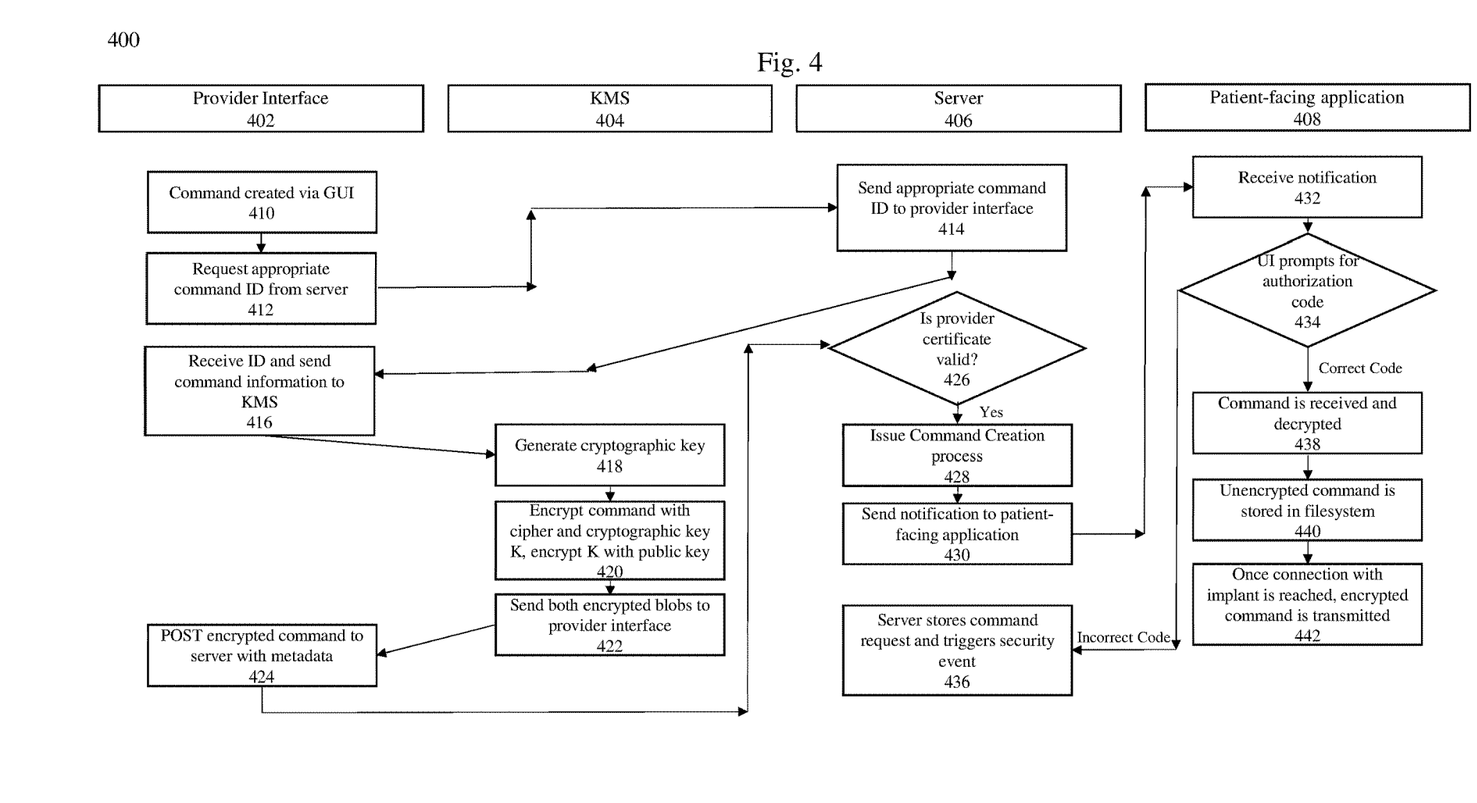
FIG. 4 is an exemplary embodiment of a method for remote commands to a medical implant.

In some embodiments an authorized person, such as for example a physician, doctor, or nurse, may be able to modify the behavior of the implanted medical device remotely. Referring now to FIG. 4. An exemplary embodiment of a method for remote commands to a medical implant 400 may be shown. In the exemplary embodiment a provider interface 402, a KMS 404, a server 406, and a patient-facing application 408 may interact in order to achieve remote command of the medical implant. In a first step 410 a user may create a command using the provider interface 402 GUI. The provider interface 402 may then request appropriate command ID information from the server 406 in step 412. The server 406 may then send the appropriate command ID to the provider interface 402 in step 414. In a next step 416 the provider interface 402 may receive the command id and then send the command data to the KMS 404, the command data may also include, for example, the intended companion device for the command. In a next step 418 the KMS may generate an ephemeral key K. In a next step 420 the KMS may encrypt the command with a cipher and with the generated key K and may encrypt the key K with a public key. In a next step 422 both sets of encrypted data may be sent back to the provider interface 402. In a next step 424 the provider interface may then post the encrypted command data to the server along with, for example, metadata, the intended companion device, an authorization code, etc.

In a next step 426 the server 406 may verify that the provider certificate given by the provider interface 402 is correct, if a valid certificate or other authentication mechanism is not provided the server may, for example, ignore the command and/or provide a security alert. If the provided certificate or other authentication mechanism is valid then in a next step 428 the server 406 may issue a command creation process. In a next step 430 the server 406 may send a notification to the patient-facing application 408, which may be received by the patient-facing application 408 in step 432. In a next step 434 for the patient-facing application UI may prompt for an authorization code. If an incorrect code is entered in step 436 the server 406 may store the command request and trigger a security event. In some embodiments the security event may only be triggered after a set number of consecutive failures, e.g. 3 failures or 5 failures. If a correct code is entered in step 434 then in a next step 438 the patient-facing application may receive and decrypt the command. In a next step 440 the unencrypted command may be stored in the patient-facing application 408's filesystem. In a final step 442 the patient-facing application may wait until there is a connection with the medical implant, and then may encrypt and transmit the encrypted command.

Figure 5:
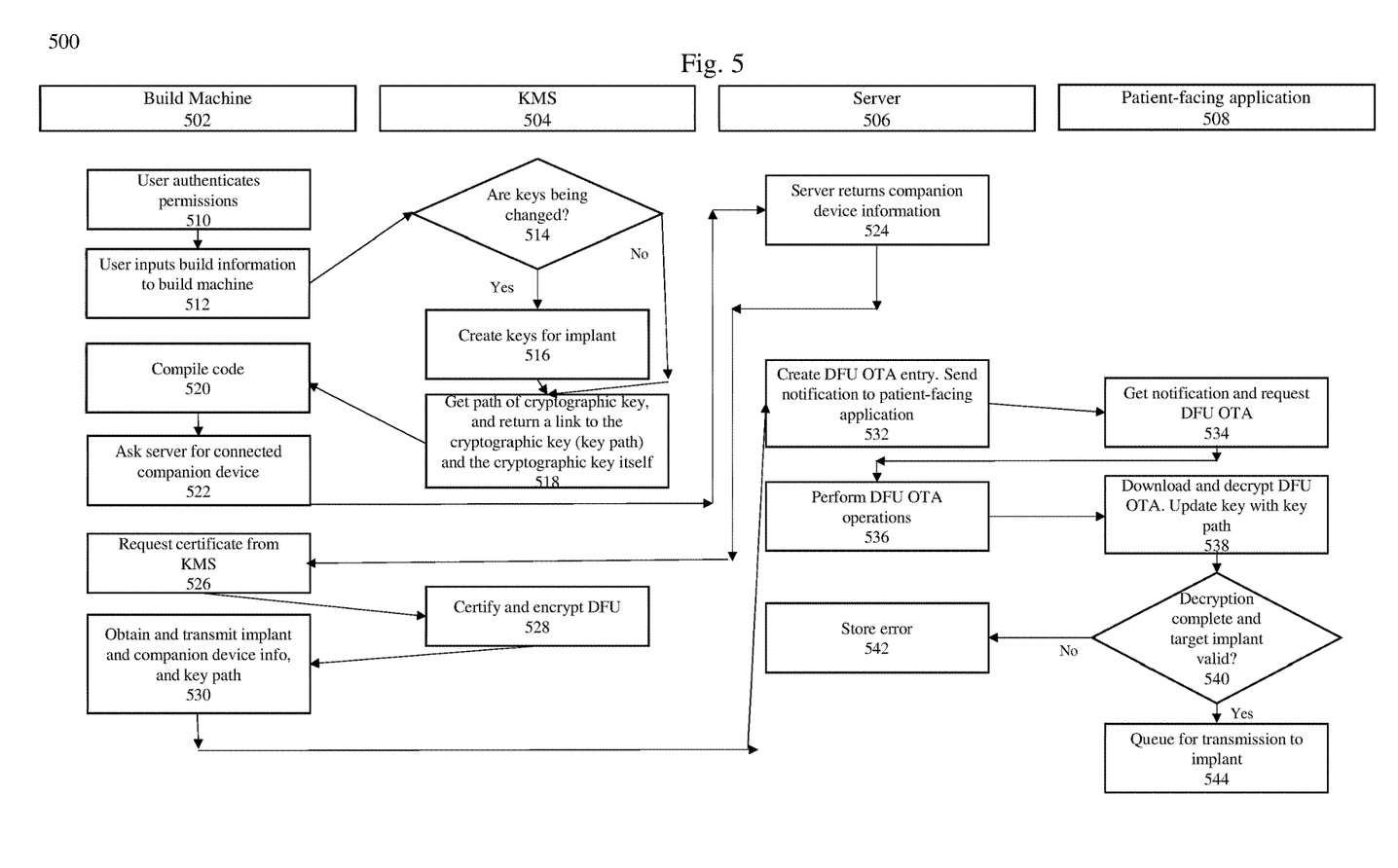
FIG. 5 is an exemplary embodiment of a method for remote updating a medical implant.

In some embodiments the above systems may allow for updating of the medical implant from any remote location, without needing physical access to the medical implant. Referring to FIG. 5 an exemplary embodiment of a method for remote updating a medical implant 500 may be shown. In the exemplary embodiment a build machine 502, a KMS 504, a server 506, and a patient-facing application 508 may interact in order to achieve remote updating of the medical implant.

In a first step 510 the user may authenticate their permissions to the build machine 502. In a next step 512 the user may input build information to the build machine. Build information may include, for example, what software version to run on the implant, the name and number of the implant or implants, whether the cryptographic key should be changed, etc. In a next step 514 the KMS may receive whether the cryptographic key should be changed or not. If the cryptographic key does need to be changed the KMS may create a new cryptographic key for the implant in step 516. Then, or if the cryptographic key doesn't need to be changed, the cryptographic key and key path may be created by the KMS in step 518 and returned to the build machine. In a next step 520 the build machine 502 may compile the code for the OTA DFU. In a next step 522 the build machine 502 may ask the server 506 for the companion device associated with the medical implant.

In a next step 524 the server 506 may return the companion device information, such as, for example, the companion device name. In a next 526 the build machine 502 may request certificate from the KMS 504. In a next step 528 the KMS 504 may certify and encrypt the DFU. In a next step 530 the build machine 502 may receive and then transmit the implant and companion device information to the server 506. In a next step 532 the server 506 may create a DFU OTA entry. In a next step 534 the server 506 may send a notification to the patient-facing application 508, which may receive the notification and request the DFU OTA. In a next step 536 the server may perform DFU OTA operations, which may include, for example, proxying the DFU OTA, updating the implant's DFU OTA status, requesting the cryptographic key if necessary, etc. In a next step 538 the patient-facing application 508 may download and decrypt the DFU OTA. In a next step 540 the patient-facing application 508 may verify that decryption was successfully completed, and the medical implant targeted for update is a valid target. If decryption was not successful, or the targeted implant is invalid, then the error may be stored in the server 506 in step 542, and additionally an alert may be sent to a user. If the decryption was successful and the targeted implant is valid, then the patient-facing application 508 may queue the DFU for transmission to the implant.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for remotely updating a medical device, comprising:
   providing build information to a build machine;
   receiving cryptographic key information and a key path;
   creating, by the build machine, a medical device update;
   receiving, by a server, companion device information, wherein the companion device is associated with the medical device;
   sending, from a key management system to the build machine, cryptographic certificate information;
   certifying and encrypting the medical device update, with the cryptographic key information;
   transmitting the encrypted medical device update, the key path, and companion device information to the server;
   sending a notification to a patient-facing application from the server, wherein the patient-facing application is accessed by the companion device;
   performing over the air update operations;

downloading the encrypted medical device update from the server to the patient-facing application;

updating the patient-facing application's cryptographic material using the key path;

transmitting the medical device update from the companion device to the medical device;

decrypting the encrypted medical device update on the medical device; and validating the medical device update on the medical device.

2. The method for remotely updating a medical device of claim 1, wherein transmitting the medical device update from the companion device to the implanted medical device comprises:

transmitting, by the medical device during a pre-determined transmission window, an advertising signal;

receiving the advertising signal on the companion device;

establishing a connection between the companion device and the medical device; and transmitting the medical device update from the companion device to the implanted medical device.

3. The method for remotely updating a medical device of claim 1, wherein the build information provided to the build machine is at least a number of medical devices, a medical device name, and a medical device software version.

4. The method for remotely updating a medical device of claim 1, wherein the companion device is a tablet.

5. The method for remotely updating a medical device of claim 1, wherein the over the air update operations include at least proxying the update and requesting cryptographic key information.

6. The method for remotely updating a medical device of claim 1, wherein validating the medical device update includes at least validating the source of the medical device update and ensuring the update have an increasing version number from the medical device's software current version number.

7. The method for remotely updating a medical device of claim 2, wherein the medical device is an implantable medical device.

8. The method for updating a medical device of claim 7, wherein the implantable medical device is one of a cranial implant, spine implant, or joint implant.

9. A system for remotely updating a medical device, comprising:

the medical device;

a companion device associated with the medical device;

a server that sends companion device information to a build machine;

a key management system which sends a cryptographic certificate to the build machine;

the build machine, which receives at least build information, cryptographic key information, and a key path; creates a medical device update; certifies and encrypts the medical device update with the cryptographic certificate; and transmits the medical device update and companion device information to the server;

wherein the server further sends a notification to a patient-facing application that is accessed by the companion device and performs over the air update operations;

wherein the companion device downloads the encrypted medical device update from the server and transmits the medical device update to the medical device; and wherein the medical device decrypts and validates the encrypted medical device update.

10. The system for remotely updating a medical device of claim 9, wherein the medical device transmits an advertising signal during a pre-determined transmission window; and the companion device receives the advertising signal and establishes a connection between the companion device and the medical device and transmits the medical device update from the companion device to the medical device.

11. The system for remotely updating a medical device of claim 9, wherein the build information provided to the build machine is at least a number of medical devices, a medical device name, and a medical device instance number.

12. The system for remotely updating a medical device of claim 9, wherein the companion device is a tablet.

13. The system for remotely updating a medical device of claim 9, wherein the over the air update operations include at least proxying the update and requesting cryptographic key information.

14. The system for remotely updating a medical device of claim 9, wherein validating the medical device update includes at least validating the source of the medical device update and ensuring the update have an increasing version number from the medical device's software current version number.

15. The system for remotely updating a medical device of claim 10, wherein the medical device is an implantable medical device.

16. The system for remotely updating a medical device of claim 15, wherein the implantable medical device is one of a cranial implant, spine implant, or joint implant.

\* \* \* \* \*